US00PP35317P2

(12) United States Plant Patent
Mathey

(10) Patent No.: US PP35,317 P2
(45) Date of Patent: Aug. 15, 2023

(54) ***HYDRANGEA* PLANT NAMED 'SMNHMTB'**

(50) Latin Name: *Hydrangea macrophylla*
Varietal Denomination: SMNHMTB

(71) Applicant: Spring Meadow Nursery Inc., Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/087,370

(22) Filed: Dec. 22, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHMTB' is disclosed, characterized by large, mophead inflorescences, colored hot pink to royal purple based on soil pH. Plants are truly remontant, heavily floriferous, and have dark-green foliage that turns burgundy in the fall. The new variety is a *Hydrangea*, typically produced as an outdoor ornamental plant.

4 Drawing Sheets

Latin name of the genus and species: *Hydrangea macrophylla.*

Variety denomination: 'SMNHMTB'.

BACKGROUND OF THE INVENTION

The new cultivar is a product of a planned breeding program conducted by the inventor, at a commercial nursery in Grand Haven, Mich. The objective of the breeding program was to produce truly remontant *Hydrangea macrophylla* varieties with vibrant flower coloration and a compact habit. The crossing resulting in the new variety was made during the Summer of 2015.

The seed parent is the unpatented variety *Hydrangea macrophylla*, 'Cote d'Azur'. The pollen parent is the variety *Hydrangea macrophylla*, 'Piihm-ii', U.S. Plant Pat. No. 25,566.

The new variety was found and selected by the inventor in the Summer of 2018 at the same nursery in Grand Haven, Mich.

Asexual reproduction of the new cultivar 'SMNHMTB' was first performed during the Summer of 2018 in Grand Haven, Mich., by softwood cuttings. Through subsequent asexual propagation, multiple additional generations have been reproduced, having shown that the unique features of this cultivar are stable and reproduced true to type

SUMMARY OF THE INVENTION

The cultivar 'SMNHMTB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHMTB'. These characteristics in combination distinguish 'SMNHMTB' as a new and distinct *Hydrangea* cultivar:

1. Truly remontant.
2. Vibrant flower colors (hot pink or royal purple if treated with a bluing agent).
3. Compact, mounded/rounded growth habit (maximum mature size 3-4'tall and wide).
4. Dark green foliage.
5. Foliage develops burgundy coloration in the fall.
6. Heavily floriferous (large mophead panicles on nearly every or every lateral branch).

PARENT COMPARISONS

Plants of 'SMNHMTB' are similar to plants of the seed parent in most horticultural characteristics, however, plants of 'SMNHMTB' differ in the following:

1. Panicle diameter of the new variety is larger than the panicle diameter of the seed parent.
2. Flower panicles of the new variety are more hemispherical, while flower panicles of the seed parent are more flat-bottomed.

Plants of 'SMNHMTB' are similar to plants of the pollen parent in most horticultural characteristics, however, plants of 'SMNHMTB' differ in the following:

1. Flower color of the new variety is hot pink without bluing agent, while flower color of the pollen parent is soft pink without bluing agent.

COMMERCIAL COMPARISONS

Plants of the new cultivar *Hydrangea* 'SMNHMTB' can be compared to the commercial variety *Hydrangea* 'Paris Rapa', U.S. Plant Pat. No. 10,906. Plants of 'SMNHMTB' are similar to plants of 'Paris Rapa' in most horticultural characteristics, however, plants of 'SMNHMTB' differ in the following:

1. Panicle diameter of the new variety is larger than panicle diameter of this comparator.
2. Flowers of the new variety "blue" well to a violet coloration, while flowers of this comparator "blue" to a muddy coloration.

Plants of the new cultivar *Hydrangea* 'SMNHMTB' can be compared to the commercial variety *Hydrangea* 'SMHMES14', U.S. Plant Pat. No. 25,836. Plants of 'SMNHMTB' are similar to plants of 'SMHMES14' in most horticultural characteristics, however, plants of 'SMNHMTB' differ in the following:

1. Sepal color of the new variety is vibrant red-pink in aluminum-free soil, while sepal color of this comparator is softer pink in aluminum-free soil.
2. Flowers of the new variety "blue" well to a violet coloration, while flowers of this comparator "blue" well to a bluer coloration.

BRIEF DESCRIPTION OF THE PHOTOGRAPHS

The accompanying photograph in FIG. 1 illustrates in full color a typical plant of 'SMNHMTB' grown outdoors in Grand Haven, Mich. with aluminum in the soil. This plant is approximately 2 to 3 years old.

Figure 1:
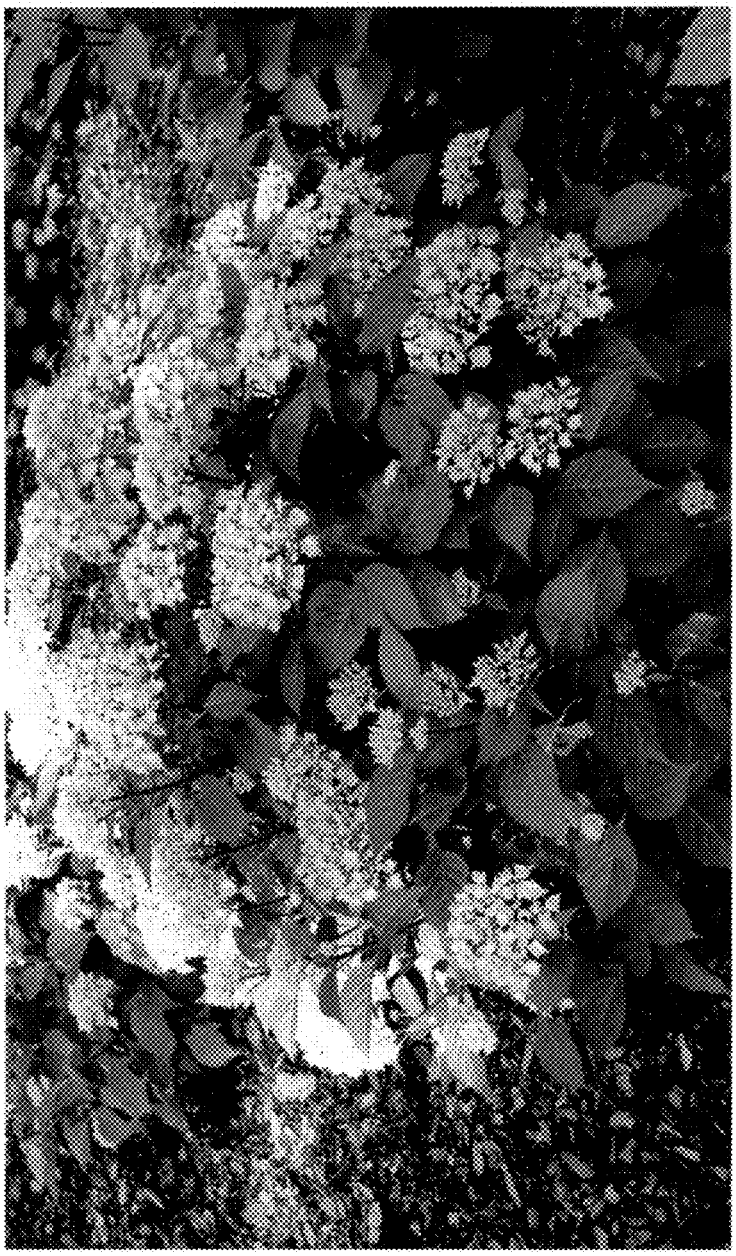
Figure 2:
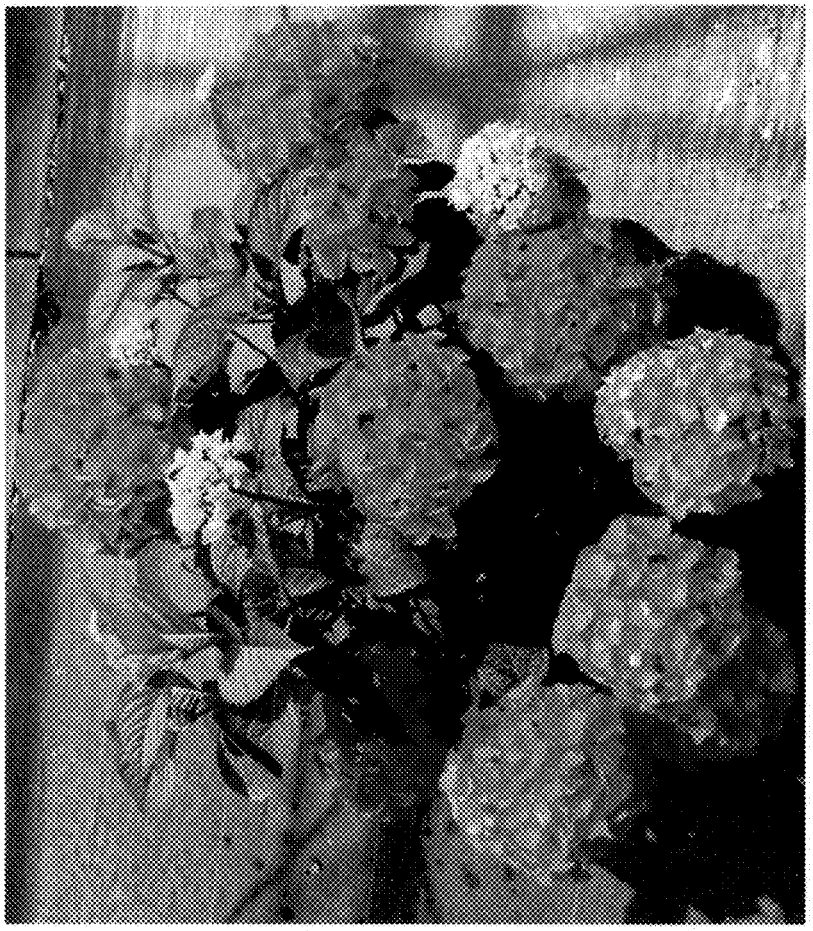
FIG. 2 illustrates in full color a typical plant of 'SMNHMTB' grown in a polyhouse in Grand Haven, Mich. with no aluminum in the soil.
Figure 3:
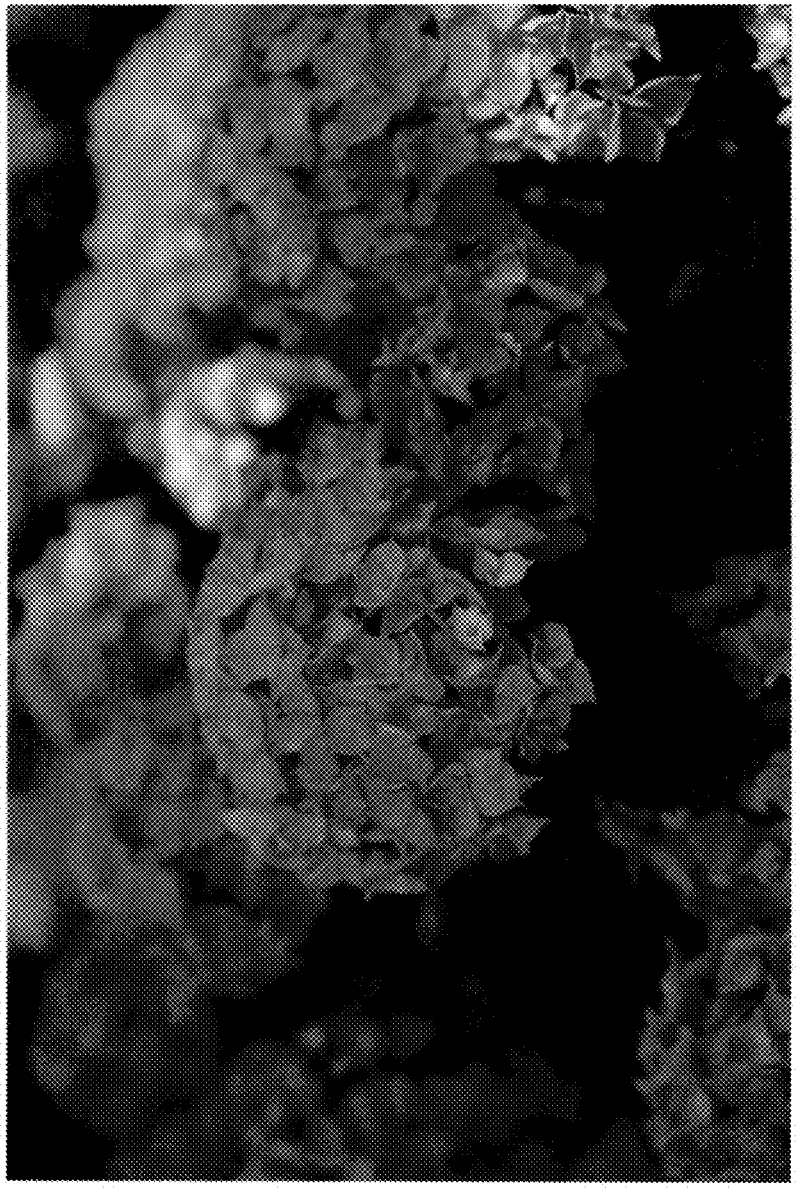
FIG. 3 illustrates in full color a close-up view of the inflorescence of the plant in FIG. 2.
Figure 4:
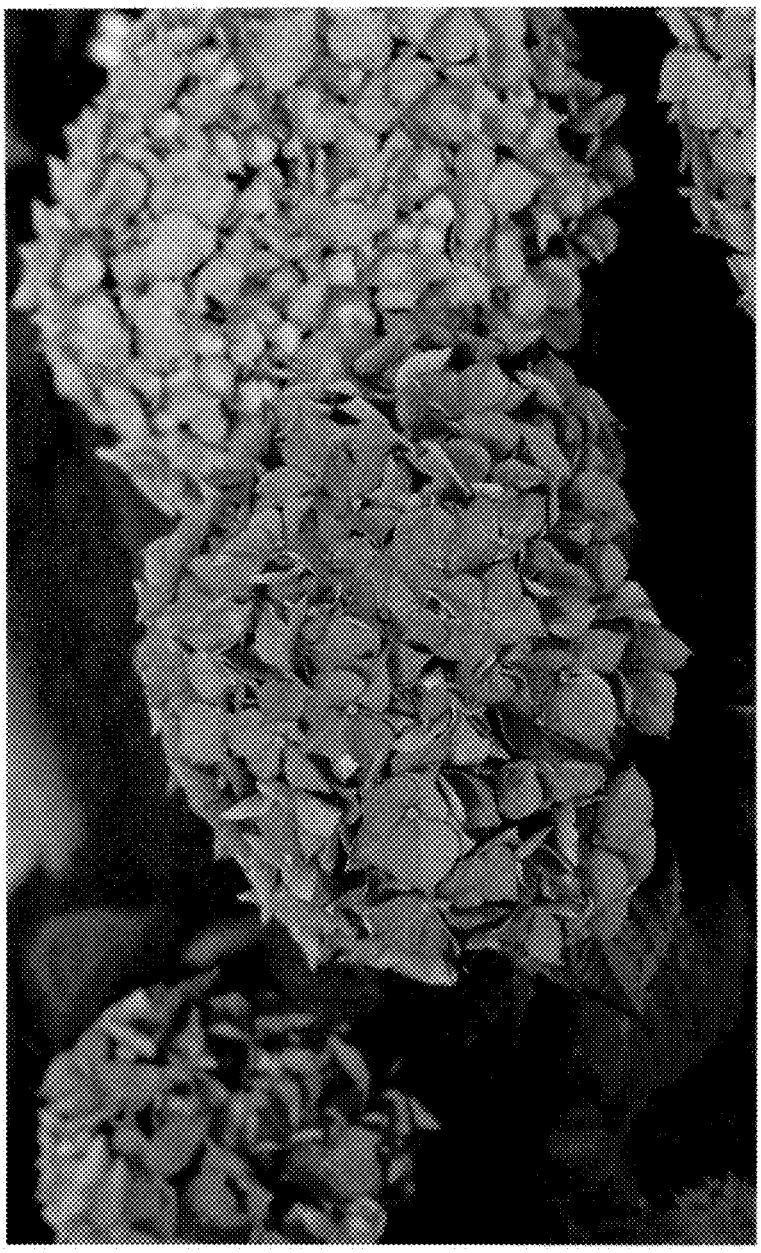
FIG. 4 illustrates in full color a close-up view of the inflorescence of the plant in FIG. 1.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNHMTB' plants grown in a poly- greenhouse in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea macrophylla* 'SMNHMTB'.

PROPAGATION

Typical method: Softwood cuttings.
Root initiation: 18 days during the summer.
Time to produce rooted cutting: 60 days during the summer.
Roots: Thick and fine, moderately branching, fibrous, moderately dense. White and brown in color, not accurately measured with R.H.S. chart.

PLANT

Growth habit: Compact, upwards and outwards.
Shape: Rounded and mounded.
Height: 50 cm.
Plant spread: 70 cm.
Pot size of plant described: 3-gallon container.
Age of plant described: Approximately 2 to 3 years.
Growth rate: Good.
Plant vigor: Moderate to fairly vigorous.
Stem:
- *Branching*.—Freely branching, mostly upward and somewhat outward. Little to no basal branching, pinching required.
- *Number of lateral branches*.—About 25.
- *Shape*.—Round with lenticels.
- *Color*.—Immature: RHS Yellow-Green 144B. Mature: RHS Yellow-Green 144B with tinges of Greyed-Orange 176B, and 176B lenticels.
- *Length*.—45 cm.
- *Width*.—5 to 7 mm.
- *Aspect*.—60 to 80°.
- *Strength*.—Good.
- *Pubescence*.—None.
- *Internode length*.—7 to 10 cm.

FOLIAGE

Leaf:
- *Arrangement*.—Opposite.
- *Shape*.—Elliptic.
- *Length*.—7.5 to 15 cm.
- *Width*.—4.5 to 8 cm.
- *Apex*.—Acuminate.
- *Base*.—Cuneate/attenuate.
- *Margin*.—Serrate/serrulate.
- *Texture of top surface*.—Smooth, coriaceous, glossy.
- *Texture of bottom surface*.—Somewhat coriaceous with ridged veins.
- *Pubescence*.—None.
- *Color*.—Young foliage upper side: RHS Green NN137A. Young foliage under side: RHS Yellow-Green 147B. Mature foliage upper side: Closest to RHS Greyed-Green N189A. Mature foliage under side: RHS Green NN137C. Fall foliage upper side: Closest to Greyed-Green N189A with a Brown 200A tint developing from leaf apex to base in response to cold temperatures. Fall foliage lower side: Green NN137C.

Venation:
- *Type*.—Pinnate.
- *Color*.—Upper side: RHS Yellow-Green 144B. Under side: RHS Yellow-Green 144B with tinges of Greyed-Orange 176B.

Petiole:
- *Length*.—2 cm.
- *Width*.—3 mm.
- *Color*.—Upper side: RHS Yellow-Green 144B. Under side: RHS Yellow-Green 144B with tinges of Greyed-Orange 176B.
- *Texture*.—Upper side: Lightly pubescent. Under side: Lightly pubescent.

INFLORESCENCE

Natural flowering season: Summer.
Inflorescence type: Mophead.
Panicle:
- *Shape*.—Hemispherical.
- *Height*.—10 to 12 cm.
- *Diameter*.—18 to 20 cm.

Fragrance: None.
Sterile flowers:
*Flowers per inflorescence.*—150 to 200.
*Aspect.*—Upright, somewhat outward.
*Shape.*—Round whorl.
*Length.*—4 to 5 cm.
*Diameter.*—4 to 5 cm.
*Depth.*—5 mm.
*Persistent or self-cleaning.*—Persistent.
Bud:
*Length.*—5 mm.
*Bud diameter.*—3 mm.
*Bud shape.*—Obovate.
*Bud color.*—Acidic: RHS Blue 100B. Basic: RHS Red-Purple 63B.
Petals:
*Number per flower.*—5.
*Arrangement.*—Whorl/stellate.
*Shape.*—Elliptic.
*Tip.*—Acute.
*Base.*—Obtuse.
*Margin.*—Entire.
*Length.*—3 mm.
*Width.*—2 mm.
*Texture.*—Upper side: Smooth. Under side: Smooth.
*Color.*—When Opening, Upper side: Acidic: RHS Blue 100B. Basic: RHS Purple 75A. When Opening, Under side: Acidic: RHS Blue 100B. Basic: RHS Purple 75A. Fully Opened, Upper side: Acidic: RHS Blue 100B. Basic: RHS Purple 75A. Fully Opened, Under side: Acidic: RHS Blue 100B. Basic: RHS Purple 75A.
Sepal:
*Number.*—4 to 5.
*Arrangement.*—Cruciform/stellate.
*Shape.*—Orbicular to deltoid.
*Tip.*—Acute.
*Base.*—Cuneate.
*Margin.*—Entire.
*Length.*—2.5 cm.
*Width.*—2.25 cm.
*Texture.*—Upper side: Somewhat coriaceous, smooth. Under side: Smooth, a little leathery.
*Color.*—When Opening, Upper side: Acidic: RHS Green-White 157A with tips and upper margins tinted Violet-Blue 94B. Basic: RHS Green-White 157A with tips and upper margins tinted Red-Purple 63A and 63B. When Opening, Under side: Acidic: RHS Green-White 157A. Basic: RHS Green-White 157A. Fully Opened, Upper side: Acidic: RHS Violet-Blue 97A. Basic: RHS Red-Purple 70B. Fully Opened, Under side: Acidic: RHS Violet-Blue 94B with areas of Red-Purple 70B. Basic: RHS Red-Purple 63A and 63B.
Pedicel:
*Length.*—3 cm.
*Diameter.*—1.5 mm.
*Angle.*—45°.
*Strength.*—Good, somewhat flexible.
*Texture.*—Slightly pubescent.
*Color.*—Acidic: RHS Blue 103B. Basic: RHS Red-Purple 63A.
Fertile flowers:
*Flowers per inflorescence.*—75 to 100.
*Aspect.*—Upright.
*Shape.*—Stellate.
*Length.*—0.75 to 1 cm.
*Diameter.*—0.75 to 1 cm.
*Depth.*—4 mm.
*Persistent or self-cleaning.*—Self-cleaning.
Bud:
*Length.*—5 mm.
*Bud diameter.*—2.3 mm.
*Bud shape.*—Obovate.
*Bud color.*—Acidic: RHS Blue 100B. Basic: RHS Red-Purple 63B.
Petals:
*Number per flower.*—5.
*Arrangement.*—Whorl, stellate.
*Shape.*—Elliptic.
*Tip.*—Acute.
*Base.*—Obtuse.
*Margin.*—Entire.
*Length.*—3 mm.
*Width.*—2 mm.
*Texture.*—Upper side: Smooth. Under side: Smooth.
*Color.*—When Opening, Upper side: Acidic: RHS Blue 100B. Basic: RHS Red-Purple 63A and 63B. When Opening, Under side: Acidic: RHS Blue 100B. Basic: RHS Red-Purple 63A and 63B. Fully Opened, Upper side: Acidic: RHS Blue 100B. Basic: RHS Red-Purple 63A and 63B. Fully Opened, Under side: Acidic: RHS Blue 100B. Basic: RHS Red-Purple 63A and 63B.
Sepal: None.
Pedicel:
*Length.*—5 mm.
*Diameter.*—1 mm.
*Angle.*—45°.
*Strength.*—Good, flexible.
*Texture.*—Slightly pubescent.
*Color.*—Acidic: RHS Blue 103B. Basic: RHS Red-Purple 63A.

REPRODUCTIVE ORGANS

Sterile flower:
Stamens:
*Number.*—About 8.
*Filament color.*—Acidic: RHS Blue 102A. Basic: RHS Red-Purple 63A and 63B.
*Filament length.*—5 mm.
Anthers:
*Length.*—1 mm.
*Shape.*—Rounded, basifixed.
*Color.*—Acidic: RHS Blue 102A. Basic: RHS Green 131A.
*Pollen amount.*—Moderate.
*Pollen color.*—RHS White NN155A.
Pistil:
*Number.*—1.
*Length.*—2.5 mm.
Stigma:
*Shape.*—3-lobed.
*Color.*—Acidic: RHS Blue 100A. Basic: RHS Red-Purple 63A.
*Style length.*—1 mm.
*Style color.*—Acidic: RHS Blue 100A. Basic: RHS Red-Purple 63B.

Other sterile flower characteristics: Darker veining on the underside of fully opened sepals.

*Acidic*.—RHS Blue 103B.

*Basic*.—RHS Red-Purple 63A and 63B.

Fertile flower:

Stamen:

*Number*.—About 8.

*Filament length*.—5 mm.

*Filament color*.—Acidic: RHS Blue 102A. Basic: RHS Red-Purple 64B.

Anther:

*Shape*.—Rounded, basifixed.

*Length*.—1 mm.

*Color*.—Acidic: RHS Blue 102A. Basic: RHS Purple N77C.

*Pollen amount*.—Moderate.

*Pollen color*.—RHS White NN155A.

Pistil:

*Number*.—1.

*Length*.—2.5 mm.

Stigma:

*Shape*.—3-lobed.

*Color*.—Acidic: RHS Blue 100A. Basic: RHS Red-Purple 63A.

*Style length*.—1 mm.

*Style color*.—Acidic: RHS Blue 100A. Basic: RHS Red-Purple 63B.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −32° C. and tolerates an upper temperature range to at least 36° C.

Fruit/seed production: Not observed to date.

What is claimed is:

1. A new and distinct cultivar of *Hydrangea* plant named 'SMNHMTB' as herein illustrated and described.

* * * * *